United States Patent [19]

Schlesinger

[11] 3,990,454
[45] Nov. 9, 1976

[54] CATHETER YOKE

[76] Inventor: Robert M. Schlesinger, 43 Sumner Road, Brookline, Mass. 02146

[22] Filed: Feb. 27, 1976

[21] Appl. No.: 662,128

Related U.S. Application Data

[63] Continuation of Ser. No. 523,713, Nov. 14, 1974, abandoned.

[52] U.S. Cl. ................... 128/349 R; 128/DIG. 26; 128/133; 248/75; 248/205 A
[51] Int. Cl.² ........................................ A61M 25/02
[58] Field of Search ........................ 128/348–351, 128/133, DIG. 26, 206, 208; 248/75, 205 A

[56] References Cited
UNITED STATES PATENTS

| | | |
|---|---|---|
| 3,161,199 | 12/1964 | Shaw.................................... 128/348 |
| 3,338,538 | 8/1967 | Roche................................... 248/75 |
| 3,702,612 | 11/1972 | Schlesinger..................... 128/350 R |
| 3,782,388 | 1/1974 | Page .................................. 128/348 |
| 3,834,380 | 9/1974 | Boyd.................................... 128/133 |

*Primary Examiner*—Dalton L. Truluck
*Attorney, Agent, or Firm*—Cesari and McKenna

[57] ABSTRACT

An inexpensive catheter restraint is formed from a thin, flexible, adhesively-backed plastic sheet having a pair of short, parallel slits forming a centrally disposed bridge anchoring a catheter-receiving ring or yoke therein. The ring restrains transverse catheter motion but accommodates limited longitudinal motion.

8 Claims, 3 Drawing Figures

CATHETER YOKE

This is a continuation of application Ser. No. 523,713 filed Nov. 14, 1974, and now abandoned.

BACKGROUND OF THE INVENTION

1. Field of the Invention

The invention relates to catheter restraints and comprises a simple, inexpensive catheter restraint.

2. Prior Art

Catheters are fluid channels used to drain fluids from, or supply them to, a patient's body. Generally, these channels are in the form of extended cylindrical conduits of a limp, non-self supporting nature.

Once a catheter is inserted into a patient's body it is necessary to immobilize it relative to the body to thereby prevent its inadvertent withdrawal. Usually, this is accomplished by fixing the catheter to the body at one or more places with strips of adhesive tape. Unless a substantial length of tape is used, the attaching surface is often small and the catheter often works itself loose, thereby imposing the possibility of danger to the patient. Further, when the catheter is to be removed and reinserted, as is frequently required when the patient is examined or when the catheter is readjusted, the adhesive strips must be torn loose and replaced, thereby causing discomfort to the patient. Even minor adjustments of the catheter may require the removal and reapplication of the attaching tape, and this is a source of added inconvenience, as well as discomfort to the patient.

The disadvantages of this type of catheter attachment can be alleviated in great part by the restraint I have developed which is described in detail in U.S. Pat. No. 3,702,612 entitled "Catheter Support" and issued to me on Nov. 14, 1972. The device described therein utilizes a flexible beam attached to a supporting base plate which is secured to a patient's skin. The beam includes a catheter-receiving yoke which resists transverse motion while accommodating a limited amount of longitudinal motion. This device will be found highly desirable for many applications; however, it is desirable to provide an even less expensive restraint without undergoing any serious sacrifice of the advantages of this device.

BRIEF DESCRIPTION OF THE INVENTION

A. Objects of the Invention

Accordingly, it is an object of the invention to provide an improved catheter restraint.

Further, it is an object of the invention to provide an improved catheter restraint which firmly secures a catheter to the body of a patient while readily accommodating minor adjustment of the catheter on its axis.

A further object of the invention is to provide an inexpensive catheter restraint which allows ready withdrawal and reinsertion of the catheter.

B. Brief Description of the Invention

The catheter restraint of the present invention is formed from a thin, flat, flexible, generally circular base of substantial surface area having an adhesive coating on one face thereof for attachment to the body of the patient. Spaced parallel slits extend through the central portion of the base to form a bridge which secures a catheter-receiving yoke to the base. The yoke is in the form of a cylindrical ring which is split to allow passage of the bridge through its central portion to thereby secure the ring to the base.

In the preferred embodiment of the invention, the inner diameter of the ring is slightly smaller than the outer diameter of the cathether which it is to secure. The ring thus presses inwardly on the catheter when the catheter is placed therein and frictionally engages it with a force which is sufficient to secure it against disturbance under normal conditions, but which allows movement of the catheter through the ring when it is desired to readjust the catheter position or to withdraw it or reinsert it.

The catheter restraint of the present invention provides a substantial surface area for securing the catheter to the patient's body; thus, it is unlikely that it will be pulled from the patient's body by inadvertent movement. Further, it provides the necessary restraint for the catheter, while facilitating temporary detachment of the catheter and its reinsertion; this is accomplished without removing the restraint from the patient's body. Finally, the catheter restraint of the present invention is quite inexpensive to manufacture, and this greatly adds to its attractiveness.

DETAILED DESCRIPTION OF THE INVENTION

The foregoing and other and further objects and features of the present invention will be more readily understood on reference to the following detailed description of the invention, when taken in conjunction with the accompanying drawings in which.

Figure 1:
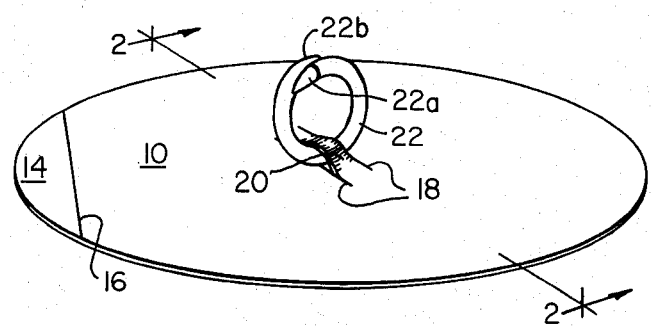
FIG. 1 is a view in perspective of a catheter restraint in accordance with the present invention.

In FIG. 1, a catheter restraint is formed from a thin, flexible generally circular base 10 having a layer 12 of adhesive applied to a reverse face thereof and backed by a release sheet 14. The base 10 is preferably formed from a thin sheet of a plastic material. In the preferred embodiment it has a diameter of approximately 2 inches. The release sheet 14 is of a treated material which is compatible with the characteristics of the adhesive 12 so as to be readily detached from it without stripping the adhesive from the sheet 10 during its detachment. Until it is so detached, it guards the adhesive layer 12 so as to prevent its adherence to undesired objects with which it may come in contact. To facilitate removal of the sheet 14, an arcute portion 16 of the base 10 is removed to expose a portion of the sheet 14 which is then readily grasped for detachment from the base 10.

Figure 1A:
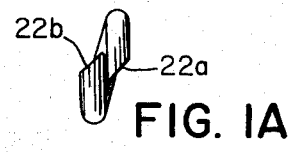
FIG. 1A is a vertical view of the catheter-securing ring of the restraint.
Figure 2:
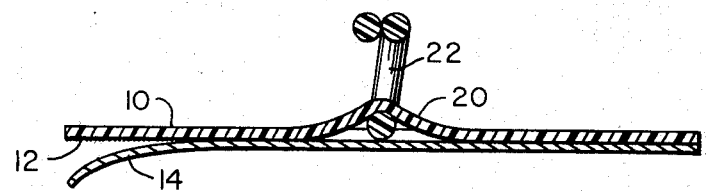
FIG. 2 is a vertical sectional view of the restraint along the lines 2—2 of FIG. 1.

Spaced parallel slits 18 of limited extent are centrally disposed on base 10 and extend through the base from one face thereof to the other. These slits define on the base a bridge 20 which secures a split, cylindrical ring or yoke 22. The ring 22 (shown in more detail in FIG. 1A) preferably has canted faces 22A, 22B formed by cutting through one part of the ring at an acute angle to the plane of the ring. The ring is then affixed to the base 10 by spreading apart the ends 22A, 22B of the ring, elevating the bridge 20 from above the base 10, and slipping one end of the ring under the bridge, from one side to the other, to thereby encompass the bridge within the ring. The ring may then be firmly secured against inadvertent removal by moving one end (e.g. 22A) to the opposite side of the other (22B) as shown in FIGS. 1 and 1A. The diameter of the ring is slightly larger than that of the catheter it is to accommodate so that the ring snugly encompasses it.

In use, a catheter is pulled through the ring 22 and inserted in the patient in the desired position. The base 10 is next located at the position at which it is desired to restrain the catheter. The release sheet 14 is then peeled off to expose the adhesive layer 12, and the base 10 is pressed firmly against the body of the patient to secure the restraint to it.

Because of its large surface contact area, the restraint can accommodate a substantial force without inadvertent removal. However, it can readily be peeled off from the patient's body when it is desired to remove it. The catheter can be removed for inspection of the patient, or for respositioning, separately from the restraint, and reinserted again in the patient without disturbing the restraint or removing it from the patient. Further, the catheter can be moved in a direction transverse to the plane of the ring (longitudinally) a desired amount, while still being restrained from movement side to side (laterally). Longitudinal freedom of the catheter is desirable, for example, in draining a deep wound; the catheter is moved outwardly of the wound in small increments as the wound progressively heals. As was previously noted, adhesive strips have heretofore been used to secure the catheter and it was thus necessary to detach these strips from the patient in order to free the catheter for movement; subsequently, they were again adhered to the patient. This was frequently quite irritating to the patient. With the present catheter restraint however, the catheter may be removed and repositioned as frequently as desired without removing the restraint. The latter is then removed only when there is no longer any use for it.

From the foregoing, it will be seen that I have provided an improved catheter restraint. The restraint is simple and inexpensive to manufacture and yet readily accommodate the needs of medical personnel. It facilitates rapid and accurate catheter positioning and minimizes patient discomfort. It will also be understood that the foregoing description and illustration is to be taken as illustrative only, and not in a limiting sense, the scope of the invention being defined with particularity in the claims.

Having illustrated and described my invention, I claim:

1. A catheter restraint comprising
   A. a thin, flexible, body-conforming base having a first adhesively coated face for attachment to the body of a patient,
   B. means forming a bridge of material extensible from a second, opposed face of said base,
   C. a catheter receiving yoke having a portion thereof extending under said bridge and elevating it above said second face, said yoke receiving a catheter therein with a portion of the periphery of the catheter in contact with a surface of said bridge and substantially the remaining periphery of the catheter in contact with said yoke, said bridge substantially restraining said yoke against motion transverse thereto while accommodating limited motion parallel thereto.

2. A catheter restraint according to claim 1 in which said base comprises a circular disc and the adhesive coating on said base has a surface area of at least 2 square inches.

3. A catheter restraint according to claim 1 in which said base comprises a circular disc and the adhesive coating on said base has a surface area of at least 5 square inches.

4. A catheter restraint according to claim 1 in which said yoke bridge forming means comprises a bridge defined by first and second generally parallel spaced slits of limited length extending through said base from one face thereof to another.

5. A catheter restraint according to claim 4 in which said yoke comprises a circular ring.

6. A catheter restraint according to claim 4 in which said yoke comprises a split circular ring.

7. A catheter restraint, comprising
   A. a thin, flexible sheet of plastic having
      1. a first adhesively coated face for releasable attachment to the body surface of a patient, and
      2. means defining first and second generally parallel slits of limited length extending through said base from said first face to an opposed face thereof and defining a bridge elevatable above said sheet, and
   B. a catheter-receiving yoke in the form of a cylindrical ring encompassing said bridge and extending outwardly of said opposed face, said ring engaging said bridge between itself and the catheter when the catheter is inserted therein, said ring substantially restraining said catheter against motion transverse thereto while accommodating limited motion parallel thereto.

8. A catheter restraint according to claim 7 in which said sheet is in the form of a generally circular disc and in which said adhesively coated face has a surface area of at least 5 square inches.

* * * * *